United States Patent [19]

Lorenz

[11] Patent Number: 4,551,311

[45] Date of Patent: Nov. 5, 1985

[54] STERILIZER CONTAINER

[75] Inventor: Jürgen W. Lorenz, Munich, Fed. Rep. of Germany

[73] Assignee: Georg Wagner KG, Munich, Fed. Rep. of Germany

[21] Appl. No.: 442,179

[22] Filed: Nov. 16, 1982

[30] Foreign Application Priority Data

Nov. 23, 1981 [DE] Fed. Rep. of Germany ....... 3146349

[51] Int. Cl.⁴ .......................... A61L 2/06; B65D 51/16
[52] U.S. Cl. ..................................... 422/300; 220/256; 220/360; 220/371; 220/374; 422/26; 422/310
[58] Field of Search ................... 422/26, 40, 297, 300, 422/310, 101, 102; 220/255, 256, 360, 361, 371, 374; 435/296, 311

[56] References Cited

U.S. PATENT DOCUMENTS

| | | | |
|---|---|---|---|
| 1,350,304 | 8/1920 | Evslin | 422/102 X |
| 2,732,092 | 1/1956 | Lawrence | 220/371 |
| 3,858,756 | 1/1975 | Fulton | 220/374 |
| 4,105,407 | 8/1978 | Sanderson | 422/26 |
| 4,124,141 | 11/1978 | Armentrout et al. | 220/371 X |
| 4,127,216 | 11/1978 | Martin, Jr. et al. | 220/256 X |
| 4,171,061 | 10/1979 | Burroughs et al. | 220/256 |
| 4,196,166 | 4/1980 | Sanderson et al. | 422/26 X |
| 4,228,914 | 10/1980 | Sanderson | 422/310 X |
| 4,251,482 | 2/1981 | Sanderson et al. | 422/40 X |
| 4,358,908 | 11/1982 | Song | 435/311 X |
| 4,402,407 | 9/1983 | Maly | 422/300 X |

FOREIGN PATENT DOCUMENTS

2375869 7/1978 France .
2436084 9/1978 France ................................. 220/360

*Primary Examiner*—David L. Lacey
*Assistant Examiner*—Brion P. Heaney
*Attorney, Agent, or Firm*—Robert D. Yeager

[57] ABSTRACT

A sterilizer container comprising a lower base portion, cover, and an intermediate cover which is installed in a sealing manner on the inwardly drawn edge of the lower base portion. The cover includes an overlapping flange. A flow passage, leading to a tortuous path, is defined by the overlapping flange of the cover and the inwardly drawn edge of the lower base portion. The exchange of fluent media between the interior and the exterior of the container takes place through the flow passage and the tortuous path. The intermediate cover is connected with the cover in a detachable manner and has perforations in its middle segment which are covered by a filter. This filter is pushed against the peripheral segment of the intermediate cover by means of a sealing ring which is supported by the cover. The intermediate cover can be provided with valves effective in two directions in place of perforations whereby an equalization of pressure is possible. In this case, the filter is omitted.

16 Claims, 17 Drawing Figures

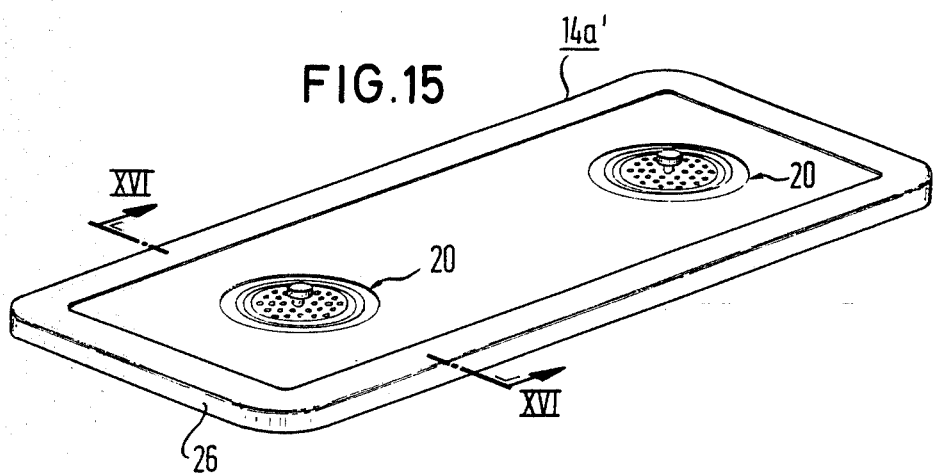
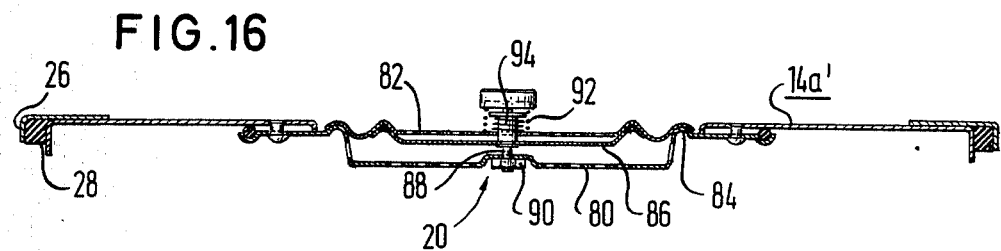
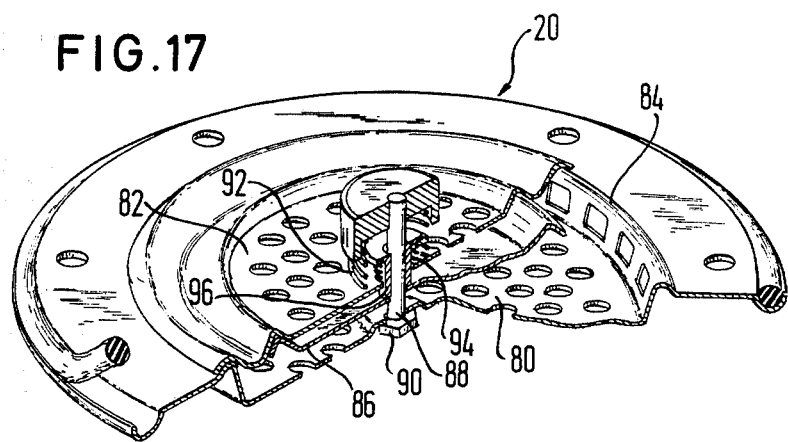

STERILIZER CONTAINER

BACKGROUND OF THE INVENTION

1. Field of the Invention

This invention relates to sterilization containers; more particularly to closable containers for holding items that are subjected to sterilization processes and for storing and transporting such items.

2. Description of the Prior Art

Containers for holding goods such as medical instruments, textiles and the like while they are subjected to sterilization processes within the chamber of a sterilizer are well known. The purpose of such containers is to provide a convenient means for storing and transporting the goods in a sterile condition, and for maintaining that sterile condition up to the time the goods are used such as, for example, when the surgeon uses a surgical instrument on a patient in the operating room.

Among the problems associated with the use of containers for the purposes just described are (i) the structure of the container must allow the interior of the container to be subjected to the same environment as that present in the sterilizer chamber during all phases of the sterilization cycle; (ii) after sterilization is complete, the interior of the container, in which sterile goods are present, must be protected against the intrusion of bacteria in any form; and (iii) the structure of the container must provide convenient operation and not be easily subjected to physical damage during handling in a way that could adversely affect the sterility of the interior.

Known sterilization containers are shown in West German Patent Application Nos. 23 01 144 and 22 07 339. Both of these containers employ filters to provide free access to the container interior by the environment within the sterilizer chamber and to block the passage of bacteria. In the former, the container cover is perforated and the filter rests beneath the perforation; in the latter, the bottom of the container is perforated and a filter rests directly on the perforated bottom.

With either arrangement just described, there exists the danger that the filter will be damaged in the area of the perforations or otherwise rendered ineffective. Mechanical damage to the filter might occur, for example, when an object is inserted through the perforations from the outside and pierces the filter. The filter also could be subjected to high dust loads or moisture, either one of which can render the filter ineffective such that bacteria can pass or grow through it. Further, the exposed filter can serve as a focal point for contamination such as drops of human saliva emitted during coughing; the bacteria present in the saliva can multiply rapidly on the filter material and thereby render the filter unusable. Any other source of droplets falling on the filter provides a source of contamination.

The known sterilization containers are subject to still further disadvantages. There is the unavoidable problem in steam sterilization processes of condensate forming when the steam contacts cool surfaces. In the case of a container with a perforated cover, such condensate forming above the cover can fall through the perforations into the container interior. The presence of this additional condensate significantly complicates the drying operation that occurs at the end of the sterilization cycle. In the case of a container with a perforated bottom, the use of a so-called "wet-covering" of disinfectant over the contaminated instruments carried in the container during transport is not possible. A "wet-cover" is often required and can be used only when the bottom of the container is waterproof.

The present invention overcomes the disadvantages associated with known sterilization containers by providing a container that is closed on all sides, yet permits free access to the container interior by the sterilizing environment and prevents the passage of microbial contamination, thereby assuring sterile storage and transporting of the container contents.

SUMMARY OF THE INVENTION

The present invention provides a sterilizing environment comprising a base portion, an intermediate cover adapted to engage the base portion in sealing relationship, the intermediate cover including means for allowing free passage of the sterilizing environment to the interior of the base portion and for preventing passage of microbial contamination thereto, an outer solid cover dimensioned to overlie the intermediate cover in spaced relationship therefrom, the space between the outer cover and the intermediate cover being in fluid communication with the sterilizing environment through a tortuous path. As used herein, the term "tortuous path" means a path available for fluid communication that includes at least one change of direction. The purpose of providing a tortuous path in the present invention is to minimize the possiblity that airborne contamination, which, of course, is subject to the force of gravity, can negotiate the available path of fluid communication from the surrounding environment to the space between the outer cover and the intermediate cover of the present invention.

In a preferred embodiment of the present invention, the outer cover includes downwardly projecting sides which together with the periphery of the base portion form an annulus that constitutes a part of the tortuous path. Preferably, the annulus is preserved by means cooperating between the downwardly projecting sides of the outer cover and the base portion.

In one embodiment of the present invention, the means for allowing free passage of the sterilizing environment and for preventing passage of microbial contamination comprises a plurality of perforations formed in the intermediate cover and a filter material covering those perforations. In an alternate embodiment, such means comprises at least one valve disposed in the intermediate cover which is otherwise solid. In a particuarly advantageous form of the present invention, intermediate covers having perforations and filter material on the one hand, and at least one valve disposed in the intermediate cover on the other hand, are interchangeable. In such advantageous embodiment, the outer cover preferably includes means for releasably engaging the intermediate cover at its periphery.

Preferably, the present invention includes a drain valve disposed in the floor of the container base portion and the floor slopes toward the drain valve. Also preferably, the present invention includes means attached to the underside of the base portion for supporting the base portion out of substantial contact with an underlying surface. Still further preferably, the present invention includes a plurality of lugs formed in the top surface of the outer cover, the lugs being registrable with the supporting means of a sterilizer container stacked above it.

BRIEF DESCRIPTION OF THE DRAWINGS

For a better understanding of the invention, reference may be had to the preferred embodiments, exemplary of the invention, shown in the accompanying drawings in which:

FIG. 15 is an isometric view of an intermediate cover for use in the present invention having two-way valves;

FIG. 16 is a sectional view taken at the plane XVI—XVI of FIG. 15; and

FIG. 17 is a partial isometric view, with parts broken away, of one of the valves shown in FIG. 15.

DESCRIPTION OF THE PREFERRED EMBODIMENTS

Figure 1:
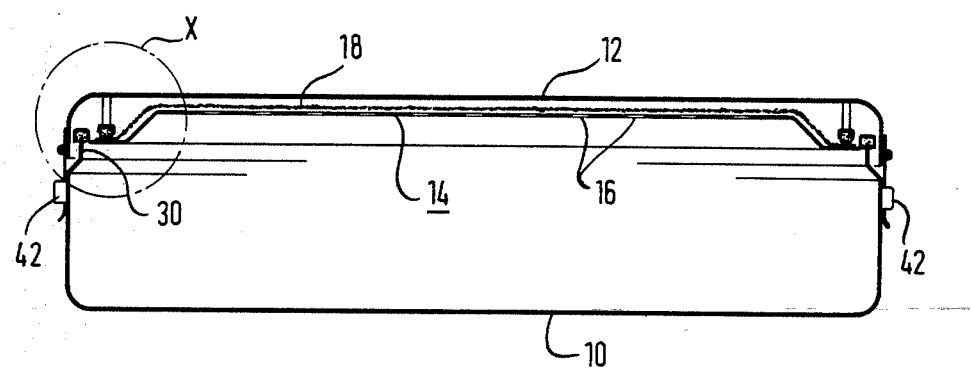
FIG. 1 is a sectional view of a sterilization container having a filter.

Referring to the drawings, the sterilizer container of the present invention includes in all embodiments a lower container portion (or base portion) 10, an outer cover 12 and an intermediate cover 14. In the embodiment shown in FIGS. 1–4, the intermediate cover 14 has perforations 16 formed therein; perforations 16 are covered by an overlying filter material 18. Filter material 18 may be formed of well-known materials that permit the passage of sterilizing media and air but prevent the passage of microbial contamination. Examples of such materials are nonwoven polyolefins, which are disposable, and 280 count muslin, which is reusable. In the embodiments shown in FIGS. 5 and 6, the intermediate cover 14a is nonperforated and has at least one two-way valve 20 installed therein. Valve 20 may be constructed in accordance with West German Pat. No. 12 17 551. In either case, intermediate covers 14, 14a ideally are interchangeable within outer cover 12.

Figure 2:
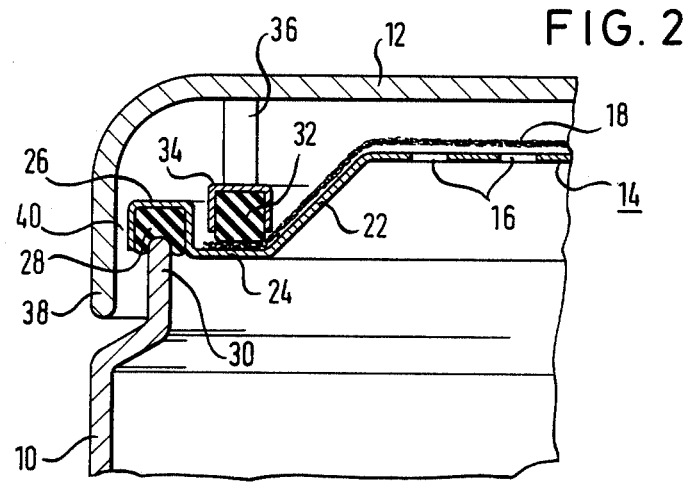
FIG. 2 is an enlarged sectional view of that portion of the container of FIG. 1 located within the circle x.

Referring to intermediate cover 14, as depicted in FIGS. 1–4, the major flat central portion contains perforations 16; proceeding toward the edges, intermediate cover 14 has an inclined transition segment 22, a flat segment 24, and terminates in an inverted U-shaped segment 26. U-shaped segment 26 is adapted to receive a sealing ring or gasket 28. In assembled condition, sealing ring 28 rests on the inwardly drawn upper edge 30 of container base portion 10. Sealing ring 28 seals the interior of container base portion 10 against the passage of microbial contamination in accordance with well-known principles. Alternatively, sealing ring 28 could be attached to upper edge 30 of container base portion 10 and form a seal with a corresponding surface of intermediate cover 14. In the embodiment shown in FIG. 2, a sealing means against the passage of microbial contamination around filter material 18 and into container base portion 10 is shown; that sealing means includes a series of downwardly extending posts 36 (only one of which is shown in FIG. 2) from the lower surface of outer cover 12. Posts 36 terminate in an inverted U-shaped segment 34 which receives sealing ring 32. The openings between posts 36 permit the free flow of sterilizing media and air. Intermediate cover 14 is releasably attached to outer cover 12 by means of screw-joints or snap closures (not shown). When outer cover 12 is placed over intermediate cover 14, seal 32 presses filter 18 in a sealing manner against flat segment 24 of intermediate cover 14. As can be seen best in FIGS. 2–4, outer cover 12 with its downwardly extending sides 38 overlaps inwardly drawn edges 30 of container base portion 10, thereby leaving an annular gap 40 through which the media exchange between the environment surrounding the sterilizer container of the present invention and the interior of container base portion 10 takes place. This arrangement, however, prevents the insertion of any objects which could damage filter 18 (or a valve as shown in FIG. 5). This arrangement further provides a tortuous path for the flow of media between the outside environment and the interior of container base portion 10. When outer cover 12 is securely fastened on container base portion 10 by means of a tension lock 42 (see FIG. 5), the interior of container base portion 10 is sealed off against microbial contamination in the manner described above. Further, the sealing ring 32 is pushed onto intermediate cover 14 and, because of the elasticity of sealing ring 32, various thicknesses of filter material 18 may be accommodated.

Figure 3:
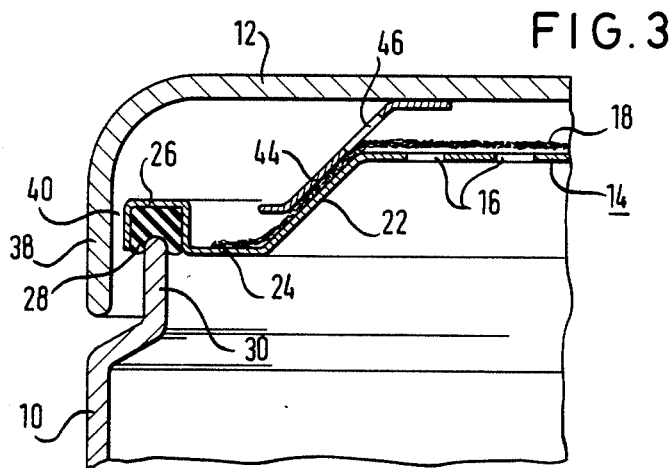
FIG. 3 is an enlarged sectional view similar to FIG. 2, of an alternate embodiment of a sterilization container.

With respect to the embodiment shown in FIG. 3, posts 36 and their associated sealing ring 32 are eliminated and replaced by a peripheral spring plate 44 which is attached to outer cover 12. Spring plate 44 is configured to conform with inclined transition segment 22 of intermediate cover 14. Spring plate 44 includes openings 46 to allow for the media exchange. The lower portion of spring plate 44 rests against filter material 18 when outer cover 12 is securely in place and presses filter material 18 against inclined transition segment 22 to effect a seal.

Figure 4:
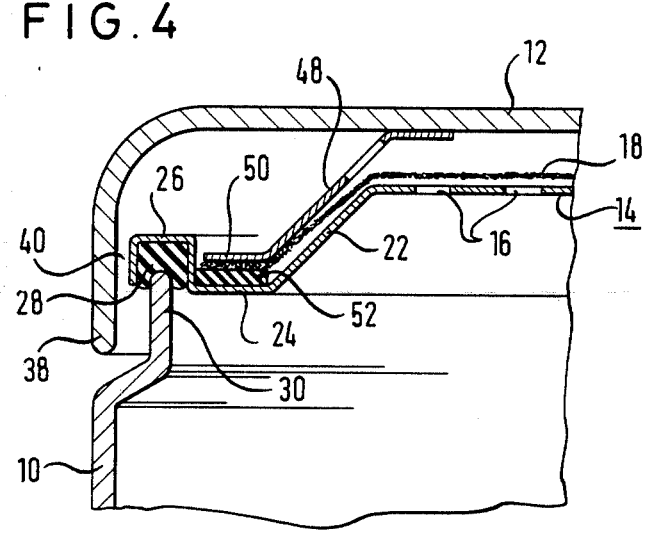
FIG. 4 is an enlarged sectional view, also similar to FIG. 2, of a still further embodiment of a sterilization container.
Figure 5:
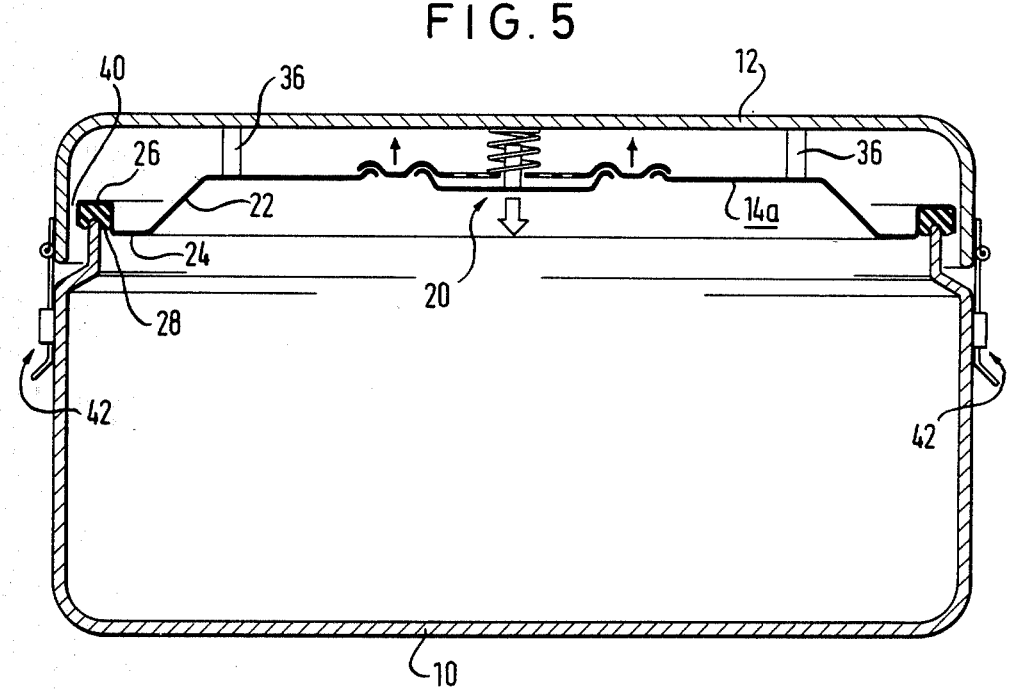
FIG. 5 is a sectional view of a sterilization container having a two-way valve.

In the embodiment shown in FIG. 4, a rigid frame 48, of similar configuration to spring plate 44, is attached to outer cover 12. Rigid frame 48 is configured to parallel inclined transition segment 22 and flat segment 24. Flat segment 24 of intermediate cover 14 has a flat sealing member 52 attached to its upper surface. In an assembled condition, flat sealing member 52 presses the edge of filter material 18 against the underside of flat peripheral segment 50 in order to prevent the passage of microbial contamination underneath filter material 18.

It thus may be seen that when outer cover 12 carrying intermediate cover 14, with filter 18, or intermediate cover 14a, with valve 20, is latched onto container base portion 10, sealing ring 28 forms a seal with edge 30 of base portion 10 and the interior of container base portion 10 is sealed off against the passage of microbial contamination.

It will be appreciated by those skilled in the art that the annulus 40 formed between outer cover 12 and the upper edges 30 of container base portion 10 will be dimensioned to permit the flow of media during all conditions, pressure or vacuum, that may be applied within a sterilizer during a sterilization cycle. The construction features of the embodiments just described assure that the media exchange will take place only through filter 18, in the case of the embodiments shown in FIGS. 1-4, or only through valve 20, in the embodiments shown in FIG. 5. These filters or valves are protected against influences from the outside by reason of the presence of overlapping outer cover 12.

Figure 6:
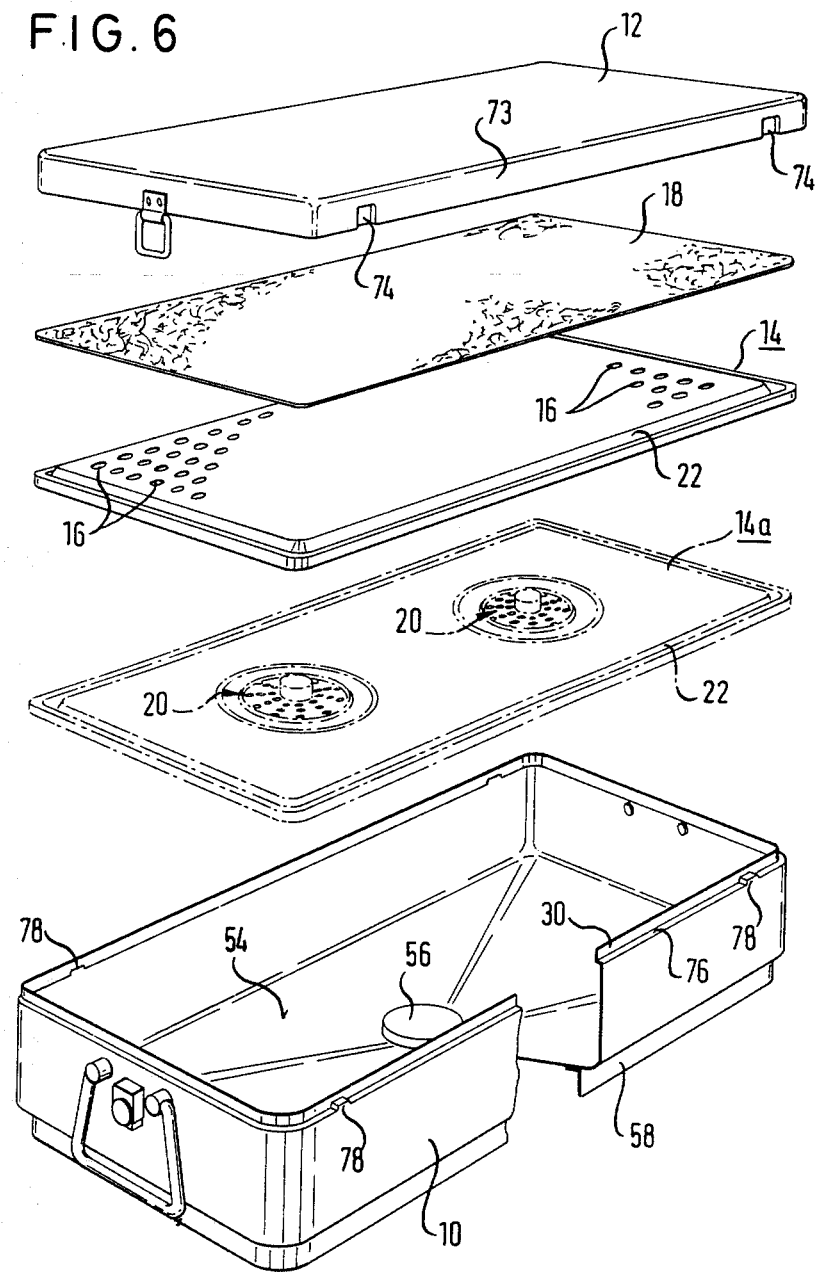
FIG. 6 is an exploded isometric view of a preferred embodiment of the present invention illustrating interchangeable intermediate covers.

FIG. 6 highlights the interchangeable nature of intermediate cover 14, which is perforated and is used in conjunction with filter material 18, and intermediate cover 14a, which is solid and includes at least one two-way valve 20. FIG. 6 also illustrates a preferred construction of container base portion 10 that includes a drain valve 56 in the floor 54 of container base portion 10. Preferably, the floor 54 is sloped downwardly in a funnel-like manner so that any condensate present within container base portion 10 can flow to drain valve 56 and be discharged therefrom. A still further preferred construction feature of container base portion 10 is illustrated in FIG. 6; namely, the presence of a peripheral base flange 58. Base flange 58 offers a number of advantages:

(1) With the floor 54 of container base portion 10 being constructed in sloping fashion, base flange 58 provides stability when container base portion 10 rests on a flat surface;

(2) Base flange 58 provides an air space between any supporting surface and floor 54 of container base portion 10 and thereby reduces the likelihood of condensate formation within container base portion 10 when it is placed on a relatively cold surface;

(3) Base flange 58 supports container base portion 10 so that drain valve 56 is out of contact with any supporting surface and thereby the likelihood of physical damage to drain valve 56 is minimized; and (4) Base flange 58 registers with the upstanding lugs formed at the corners of outer cover 12 (see FIGS. 9-12) and affords a degree alignment when sterilizer containers of the present invention are stacked.

Drain valve 56 may be of any well-known construction that opens during the sterilization cycle and closes before the sterilizer chamber is opened. Especially suited for use in the present invention as drain valve 56 is the valve described in Austrian Pat. No. 5856/80 (and corresponding West German Patent Application No. P 32 02 430.4). This latter valve has a valve disk which is carried by a bimetallic strip biased by a closing spring; in the closed position, the valve disk contacts the edge of a valve seat and is lifted from this position into the open position against the action of the closing spring upon the occurrence of temperature dependent deflection of the bimetallic strip. When the temperature falls, the bimetallic strip straightens to permit the closing spring to exert sealing pressure on the valve disk against its seat.

Figure 7:
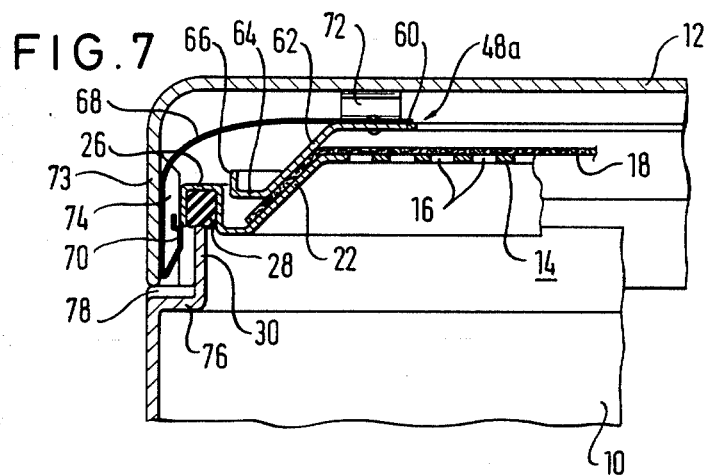
FIG. 7 is a sectional view, similiar to FIGS. 2–4, of an embodiment of the sterilization container shown in FIG. 6.
Figure 8:
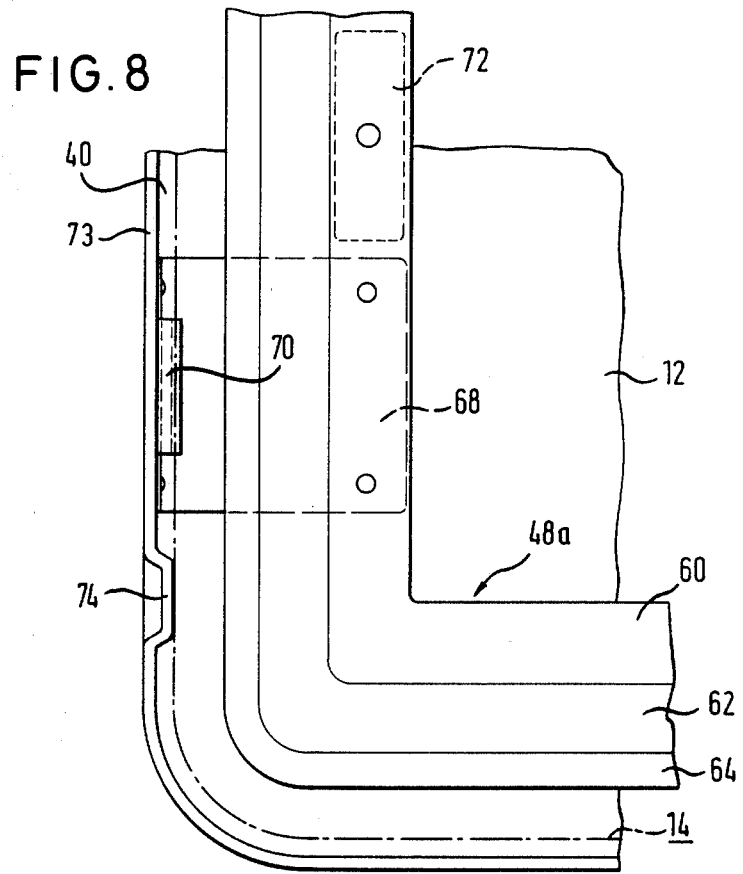
FIG. 8 is a bottom plan view of the sterilization container shown in FIG. 6.
Figure 9:
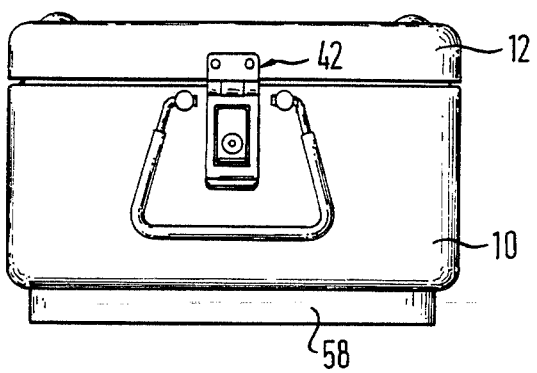
FIG. 9 is an end elevational view of the sterilization container shown in FIG. 6.
Figure 10:
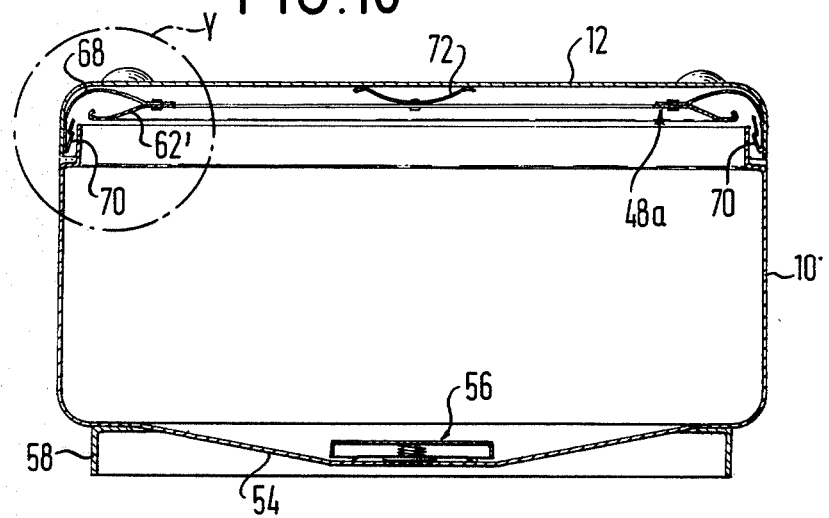
FIG. 10 is a sectional view of the sterilization container of FIG. 9 without an intermediate cover.
Figures 11, 12:
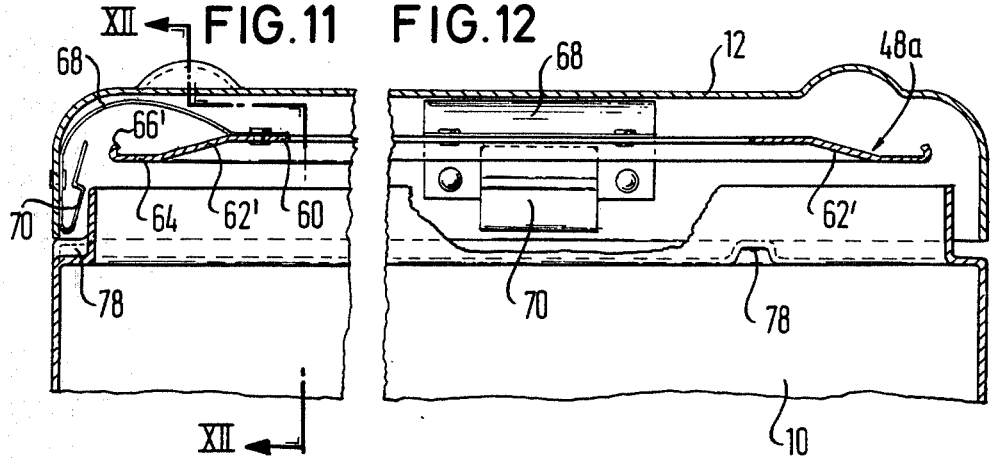
FIG. 11 is an enlarged sectional view of that portion of the sterilization container shown in FIG. 10 located within the circle y.
FIG. 12 is a sectional view taken along the line XII—XII of FIG. 11.
Figure 13:
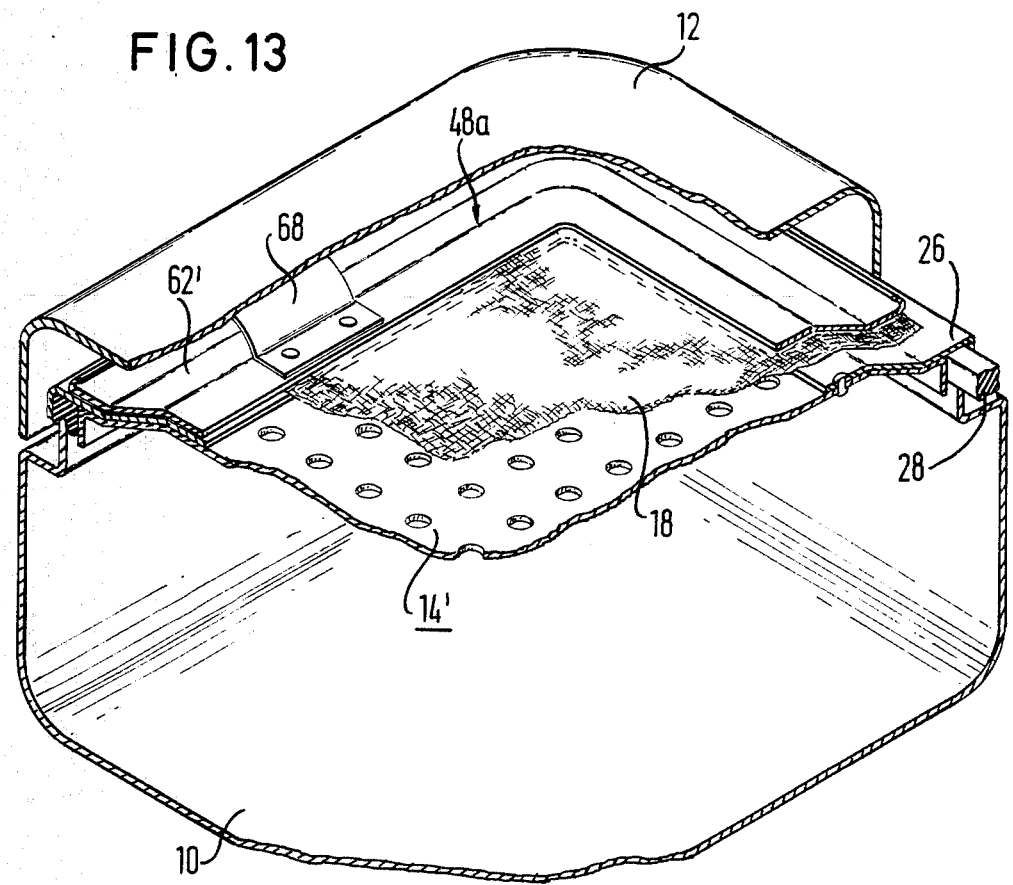
FIG. 13 is a partial isometric view, with parts broken away, of the sterilization container of the present invention having a perforated intermediate cover and a filter.
Figure 14:
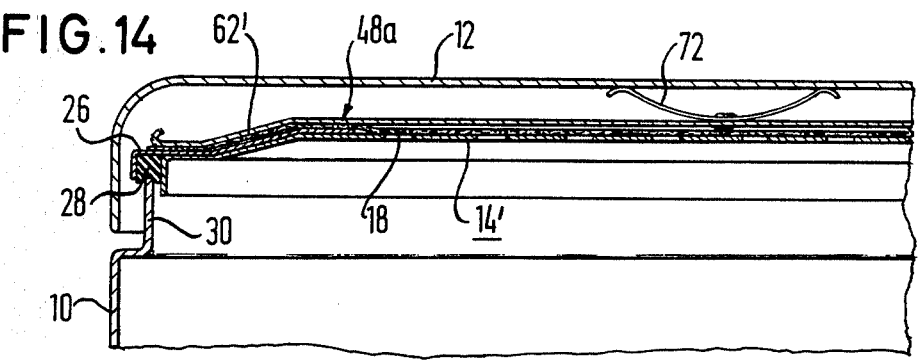
FIG. 14 is a partial sectional view of the sterilization container of FIG. 13 viewed from the left.

The embodiment of the present invention shown in FIG. 6, which advantageously permits interchangeability of intermediate cover 14 with filter material 18 and of intermediate cover 14a with valves 20, will now be described by reference to FIGS. 7-17. Referring specifically to FIGS. 7-8, a peripheral frame 48a is disposed within outer cover 12 and consists of a sheet metal section which has an inner horizontal segment 60, an inclined transition segment 62 extending downwardly and outwardly at approximately 45°, and a horizontally extending outer segment 64 which terminates in an upwardly extending flange portion 66. Frame 48a is carried inside outer cover 12 by leaf springs 68 which are either welded or riveted at one end onto the sidewalls 73 of outer cover 12 and welded or riveted at the other end to the inner segment 60 of frame 48a. The portion of leaf spring 68 contacting the sidewall 73 of outer cover 12 is bent inwardly and downwardly to terminate in a locking hook 70 which, with intermediate cover 14 in place, is positioned under the outer leg of inverted U-shaped segment 26 of intermediate cover 14; in this position, inclined transition segment 22 of intermediate cover 14 abuts transition segment 62 of support frame 48a. The engagement of inverted U-shaped segment 26 of intermediate cover 14 against locking hook 70 is effected by leaf springs 72 which are welded or riveted at their central portions to horizontal segment 60 of support frame 48a; leaf springs 72 are rounded at their two extending feet which contact the lower surface of outer cover 12 and thus serve to bias frame 48a downwardly away from outer cover 12. The sidewalls 73 of outer cover 12 are provided with inwardly extending recesses 74 which tend to center intermediate cover 14 (or 14a) within outer cover 12 and further tend to center the sidewalls 73 of outer cover 12 relative to container base portion 10 by contact of the walls of the recesses 74 with the outer edge of inverted U-shaped segment 26 of intermediate cover 14 (or 14a). In order to preserve the vertical spacing between the sidewalls 73 of outer cover 12 and the upper edges 30 of container base portion 10, ledge 76, which is formed beneath upper edge 30 of container base portion 10, has lugs 78 which register with recesses 74 when outer cover 12 is in place.

As shown in FIG. 7, an intermediate cover 14 with a filter cloth 18 is clamped into outer cover 12 as described above, with transitional inclined segments 22 and 62 of intermediate cover 14 and support frame 48a, respectively, matching and abutting one another. It will be readily apparent that in substitution for this arrangement, intermediate cover 14a with its valves 20 could be clamped within outer cover 12 by means of locking hooks 70.

The specific embodiment of the present invention shown in FIGS. 10-14, differs from the previous specific embodiments in that the transitional segment 62' of support frame 48a is made flatter to better match the surfaces of intermediate cover 14'. As shown in FIGS. 15 and 16, intermediate cover 14a' which is provided with valves 20 is removably clamped within outer cover 12 in the same manner as described for intermediate cover 14 of FIGS. 7-8 in that intermediate cover 14a' is pressed against frame 48a so that locking spring 70 can snap into position.

As shown in FIGS. 16 and 17, valve 20 of intermediate cover 14a, 14a' is a double acting closure valve which is pressure actuated. Valve 20 includes a perforated inner plate 80, a perforated outer plate 82 which abuts on a bead 84, and an inner valve plate 86; these plates are held together by means of bolt 88 and nut 90 on which a compression coil spring 92 is positioned between plate 82 and the head of bolt 88; through spring 92, outer plate 82 is pressed onto its bead seat 84. A further compression coil spring 94 is drawn over a post 96, which is fixed to valve plate 86, and spring 94 is supported between plate 82 and the head of post 96, thereby pressing valve plate 86 upwardly against plate 82.

What is claimed is:

1. A sterilizer container comprising:
a base portion having a floor and walls, thereby defining an open-topped receptacle; an intermediate cover including means to engage the periphery of the walls of said base portion in sealing relationship therewith before, during and after the container is subjected to sterilization, said intermediate cover forming with said base portion an interior chamber, and said intermediate cover including means to permit fluid communication therethrough; an outer solid cover dimensioned to overlie said intermediate cover in spaced relationship therefrom; filter means associated with said intermediate cover for preventing passage of microbial contamination into said interior chamber through said fluid communication means in said intermediate cover before, during, and after the container is subjected to sterilization; means supporting said outer cover in spaced relationship to said intermediate cover, to form a space therebetween, and in spaced relationship to said base portion engaging means; and means at the periphery of said outer cover forming with said base portion engaging means a flow passage therebetween, wherein said flow passage and the space between said intermediate cover and said outer cover define a tortuous path for the passage of an exteriorly generated sterilizing fluid to the upstream side of said filter means, the interior chamber being in fluid communication with said tortuous path through said filter means and said fluid communication means.

2. A sterilizer container as recited in claim 1 wherein: said fluid communication means includes at least one aperture formed in said intermediate cover wherein said filter means covers said aperture.

3. A sterilizer container as recited in claim 1 wherein: said base portion engaging means comprises a sealing member disposed between said intermediate cover and the periphery of the walls of said base portion.

4. A sterilizer container as recited in claim 1 wherein: said floor of said base portion includes a drain valve disposed therein.

5. A sterilizer container as recited in claim 4 wherein: said floor of said base portion slopes toward said drain valve.

6. A sterilizer container as recited in claim 1 which further comprises:
means attached to the underside of said floor of said base portion for supporting said base portion out of substantial contact with an underlying surface.

7. A sterilizer container as recited in claim 6 wherein: said supporting means comprises a downwardly extending flange member.

8. A sterilizer container as recited in claim 6 which further comprises:
a plurality of lugs formed in the top surface of said outer cover, said lugs being registrable with the supporting means of a second container.

9. A sterilizer container as recited in claim 1 wherein:
said means at the periphery of said outer cover downwardly projecting sides of said outer cover which together with for forming said flow passage comprises said base portion engaging means form an annulus that constitutes said flow passage.

10. A sterilizer container as recited in claim 9 which further comprises:
means cooperating between said downwardly projecting sides of said outer cover and said base portion engaging means for preserving said annulus.

11. A sterilizer container as recited in claim 10 wherein:
said annulus preserving means comprises a plurality of downwardly-facing recesses formed in said downwardly projecting sides of said outer cover and said walls of said base portion comprise a plurality of opposed upwardly projecting lugs, said recesses and lugs being positioned to register when said outer cover overlies said intermediate cover.

12. A sterilizer container as recited in claim 1 wherein:
said outer cover includes means for releasably engaging said intermediate cover at its periphery.

13. A sterilizer container as recited in claim 12 wherein:
said releasable engaging means comprises a frame resiliently suspended in said outer cover and having a plurality of spring clamps for engaging the periphery of said intermediate cover.

14. A sterilizer container as recited in claim 13 wherein:
said intermediate cover includes an inclined transition segment adjacent said base portion engaging means; and
said frame includes a peripheral spring plate for engaging said inclined transition segment.

15. A sterilizer container as recited in claim 14 wherein:
the periphery of said filter means are disposed between said peripheral spring plate and said inclined transition segment.

16. A sterilizer container comprising:
a base portion having a floor and walls, thereby defining an open-topped receptacle;
an intermediate cover including means to engage the periphery of the walls of said base portion in sealing relationship therewith before, during, and after the container is subjected to sterilization, said intermediate cover forming with said base portion an interior chamber;
an outer solid cover dimensioned to overlie said intermediate cover in spaced relationship therefrom;
valve means within said intermediate cover for selectively permitting the passage of fluids through said intermediate cover and into and out of said interior chamber before, during, and after the container is subjected to sterilization;
means supporting said outer cover in spaced relationship to said intermediate cover, to form a space therebetween, and in spaced relationship to said base portion engaging means; and
means at the periphery of said outer cover forming with said base portion engaging means a flow passage therebetween, wherein said flow passage and the space between said intermediate cover and said outer cover define a tortuous path for the passage of an exteriorly generated sterilizing fluid to the upstream side of said valve means, the interior chamber being in fluid communication with said tortuous path through said valve means.

* * * * *